(12) United States Patent
Kim et al.

(10) Patent No.: US 9,283,218 B2
(45) Date of Patent: Mar. 15, 2016

(54) SOLID DISPERSION WITH IMPROVED SOLUBILITY COMPRISING TETRAZOLE DERIVATIVE AS AN ACTIVE INGREDIENT

(71) Applicant: HANMI PHARM. CO., LTD., Hwaseong-si, Gyeonggi-do (KR)

(72) Inventors: Yong Il Kim, Suwon-si (KR); Jun Young Choi, Suwon-si (KR); Young Keun Choi, Daegu (KR); Jae Hyun Park, Suwon-si (KR); Jong Soo Woo, Suwon-si (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 0 days.

(21) Appl. No.: 14/439,735

(22) PCT Filed: Dec. 12, 2013

(86) PCT No.: PCT/KR2013/011545
§ 371 (c)(1),
(2) Date: Apr. 30, 2015

(87) PCT Pub. No.: WO2014/092489
PCT Pub. Date: Jun. 19, 2014

(65) Prior Publication Data
US 2015/0272943 A1 Oct. 1, 2015

(30) Foreign Application Priority Data
Dec. 13, 2012 (KR) .................. 10-2012-0145603

(51) Int. Cl.
*A61K 31/41* (2006.01)
*C07D 257/04* (2006.01)
*A61K 31/4725* (2006.01)
*C07D 405/14* (2006.01)
*C07D 401/14* (2006.01)
*C07D 405/12* (2006.01)
*A61K 45/06* (2006.01)
*A61K 31/337* (2006.01)
*A61K 31/475* (2006.01)
*A61K 31/704* (2006.01)

(52) U.S. Cl.
CPC .......... *A61K 31/4725* (2013.01); *A61K 31/337* (2013.01); *A61K 31/475* (2013.01); *A61K 31/704* (2013.01); *A61K 45/06* (2013.01); *C07D 401/14* (2013.01); *C07D 405/12* (2013.01); *C07D 405/14* (2013.01); *C07B 2200/13* (2013.01)

(58) Field of Classification Search
CPC ............................. A61K 31/41; C07D 257/04
USPC .......................................... 514/382; 548/251
See application file for complete search history.

(56) References Cited

FOREIGN PATENT DOCUMENTS

| KR | 10-2005-0038858 A | 4/2005 |
|---|---|---|
| KR | 10-0557093 B1 | 3/2006 |
| KR | 10-2007-0072888 A | 7/2007 |
| KR | 10-2011-0083870 A | 7/2011 |

OTHER PUBLICATIONS

Schinkel et al., "Disruption of the Mouse mdr1a P-Glycoprotein Gene Leads to a Deficiency in the Blood-Brain Barrier and to Increased Sensitivity to Drugs", Cell, May 20, 1994, pp. 491-502, vol. 77.
International Searching Authority, International Search Report of PCT/KR2013/011545 dated Mar. 31, 2014 [PCT/ISA/210].

*Primary Examiner* — Raymond Henley, III
(74) *Attorney, Agent, or Firm* — Sughrue Mion, PLLC

(57) ABSTRACT

The present invention relates to an amorphous solid dispersion comprising a tetrazole derivative of the formula (I) or a pharmaceutically acceptable salt thereof as an active ingredient. The solid dispersion of the present invention comprises a water-soluble polymer or an acid so as to improve the solubility of its active ingredient, i.e., the tetrazole derivative of the formula (I), thereby improving its absorption rate, and thus can be effectively used to reduce multi-drug resistance (MDR) in cancer cells.

20 Claims, 3 Drawing Sheets

SOLID DISPERSION WITH IMPROVED SOLUBILITY COMPRISING TETRAZOLE DERIVATIVE AS AN ACTIVE INGREDIENT

CROSS REFERENCE TO RELATED APPLICATIONS

This application is a National Stage of International Application No. PCT/KR2013/011545, filed Dec. 12, 2013, claiming priority based on Korean Patent Application No. 10-2012-0145603, filed Dec. 13, 2012, the contents of all of which are incorporated herein by reference in their entirety.

FIELD OF THE INVENTION

The present invention relates to a solid dispersion with improved solubility comprising a tetrazole derivative as an active ingredient, more particularly, an amorphous solid dispersion comprising a tetrazole derivative of the formula (I) or a pharmaceutically acceptable salt thereof as an active ingredient, and a pharmaceutical formulation comprising the same.

BACKGROUND OF THE INVENTION

The following tetrazole derivative of the formula (I) and a pharmaceutically acceptable salt thereof are known as a p-glycoprotein inhibitor, which has inhibitory activities on multidrug resistance in cancer cells (see KR Pat. No. 10-0557093):

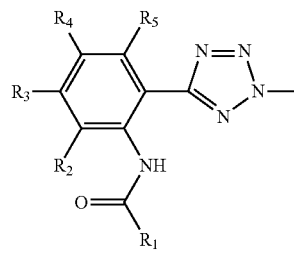

wherein $R_1$ to $R_{11}$, m, n and X are the same as defined below.

P-glycoproteins are found in endothelial cells of the gastrointestinal tract, etc., and they are known to limit oral absorption of certain drugs. Some of the major anti-cancer agents such as paclitaxel, docetaxel and the like cannot be absorbed by the body mostly, because of the action of P-glycoprotein, if they were administered orally (Schinkel et al., *Cell*, 77, 491-502, 1994). One of the critical problems in the anti-cancer therapy is the expression of resistance towards anti-cancer agents in cancer cells and, among them, the most critical problems are multi-drug resistance (MDR) caused by overexpression of P-glycoprotein. In general, MDR in cancer cells increases as the use of anti-cancer agent increases, and this is a causative factor which substantially lowers cancer survival rates.

Accordingly, the P-glycoprotein inhibitor comprising a tetrazole derivative of the formula (I) can inhibit the action of the P-glycoprotein, thereby allowing oral administration of certain drugs and, thus, it is expected to be effective against the MDR in cancer cells that is induced by overexpression of P-glycoprotein.

Nevertheless, a tetrazole derivative and a pharmaceutically acceptable salt thereof have very low solubilities, and thus it is difficult to expect good in vivo absorption rate. Therefore, there is a need for improving the solubility and in vivo absorption rate of the aforementioned drug.

SUMMARY OF THE INVENTION

Accordingly, it is an object of the present invention to improve solubility and in vivo absorption rate of the aforementioned tetrazole derivative and a pharmaceutically acceptable salt thereof.

In accordance with one object of the present invention, there is provided an amorphous solid dispersion comprising a tetrazole derivative of the formula (I) or a pharmaceutically acceptable salt thereof as an active ingredient, and a pharmaceutical formulation comprising the same:

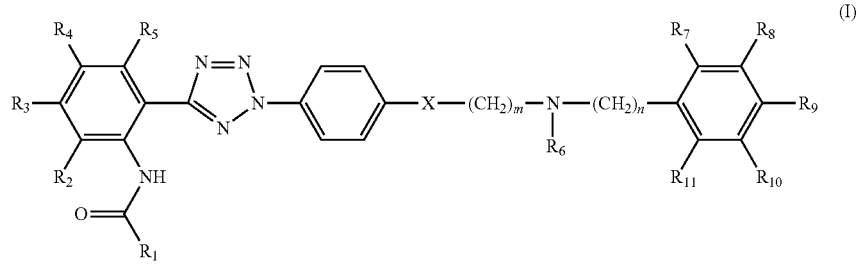

wherein, $R_1$ is quinoline, isoquinoline, quinoxaline, pyridine, pyrazine, naphthalene, phenyl, thiophene, furan, 4-oxo-4H-chromene or cinnoline, which is unsubstituted or substituted by $C_1$-$C_5$alkyl, hydroxyl, $C_{1-5}$alkoxy, halogen, trifluoromethyl, nitro or amino;

$R_2$ to $R_5$ and $R_8$ to $R_{11}$ are each independently H, hydroxyl, halogen, nitro, $C_1$-$C_5$alkyl or $C_{1-5}$alkoxy; $R_6$ and $R_7$ are each independently H, hydroxyl, halogen, nitro, $C_{1-5}$alkylene or $C_{1-5}$alkoxy; and $R_6$ and $R_7$ may be connected to form a 4- to 8-membered ring;

m and n are each independently integers ranging from 0 to 4; and

X is $CH_2$, O or S.

The inventive solid dispersion comprises a water-soluble polymer and/or an acid so as to improve the solubility of its active ingredient, i.e., the tetrazole derivative of the formula (I), thereby improving in vivo absorption rate thereof, and thus can be effectively used to reduce MDR in cancer cells.

DETAILED DESCRIPTION OF THE INVENTION

Figure 1:
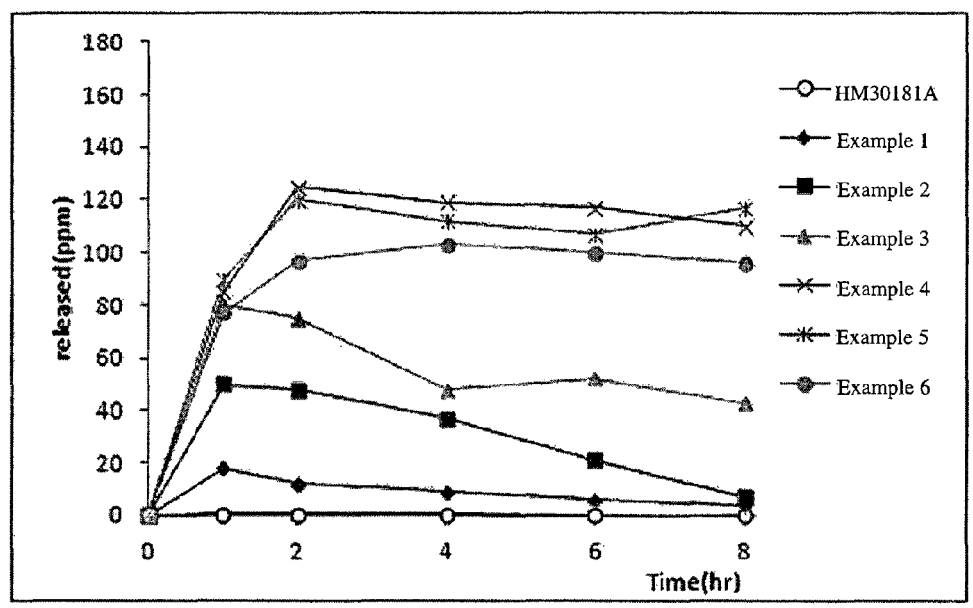
FIG. 1 is a graph showing the solubilities of HM30181A, a tetrazole derivative of the formula (I), and the solid dispersions comprising HM30181A and different amounts of water-soluble polymer (Examples 1 to 6).

Hereinafter, the present invention is described in detail.

The present invention provides an amorphous solid dispersion comprising a tetrazole derivative of the formula (I) or a pharmaceutically acceptable salt thereof as an active ingredient.

The tetrazole derivative of the formula (I) or a pharmaceutically acceptable salt thereof, the method for manufacturing the same, and the use thereof are disclosed in KR Pat. No. 10-0557093.

In accordance with one specific embodiment of the present invention, the tetrazole derivative may be the compound of formula (II), chromone-2-carboxylic acid [2-(2-{4-[2-(6,7-dimethoxy-3,4-di-hydro-1H-isoquinolin-2-yl)-ethyl]-phenyl}-2H-tetrazol-5-yl)-4,5-dimethoxyphenyl]amine mesylate, or the compound of formula (III), chromone-2-carboxylic acid [2-(2-{4-[2-(6,7-dimethoxy-3,4-di-hydro-1H-isoquinolin-2-yl)-ethyl]-phenyl}-2H-tetrazol-5-yl)-4,5-dimethoxyphenyl]amine:

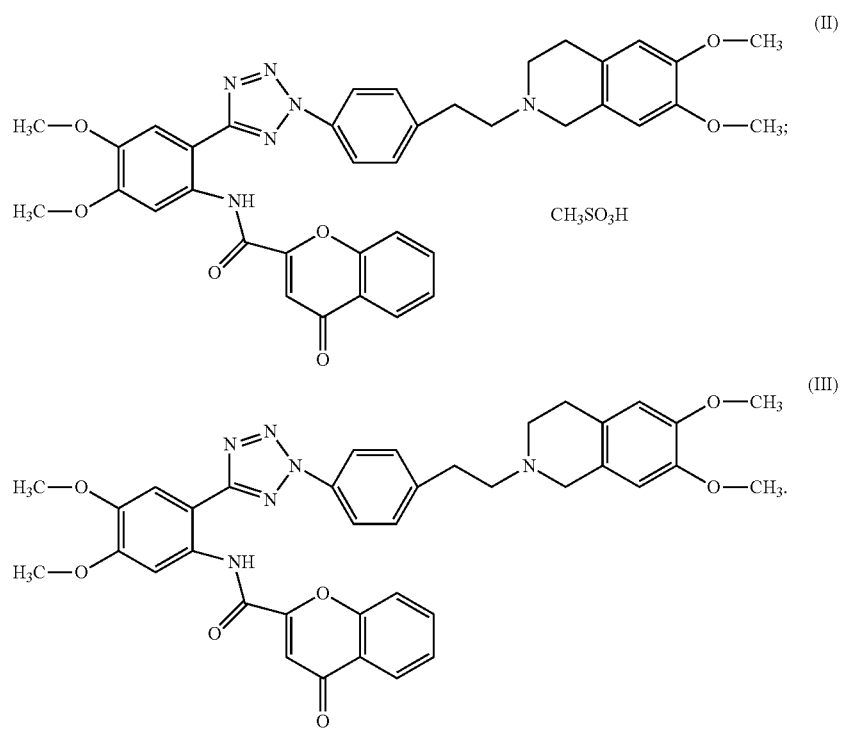

The solid dispersion of the present invention may be obtained by dissolving the tetrazole derivative of the formula (I) or a pharmaceutically acceptable salt thereof in a solvent, preferably an organic solvent, to form a mixed solution, and then removing the solvent by using a conventional method, preferably spray drying method.

The solid dispersion of the present invention may further comprise a water-soluble polymer besides the active ingredient so as to enhance the solubility of the tetrazole derivative of the formula (I) or a pharmaceutically acceptable salt thereof.

When the solid dispersions are prepared from the tetrazole derivative or a pharmaceutically acceptable salt thereof, the water-soluble polymer acts as a water-soluble carrier to make the active ingredient hydrophilic, thereby improving its solubility, and it also helps maintaining the solid dispersions in an amorphous state. Examples of the water-soluble polymers include hypromellose, hydroxypropyl cellulose, polyvinylpyrrolidone, polyvinyl acetal, diethyl aminoacetate, polyethylene glycol or a mixture thereof, but not limited thereto. In one preferable embodiment of the present invention, hypromellose is used when the solid dispersions are prepared from the tetrazole derivative or a pharmaceutically acceptable salt thereof.

The water-soluble polymer may be included in an amount of 0.1 to 4 parts by weight, based on 1 part by weight of the active ingredient. When the water-soluble polymer is used in an amount of 4 parts by weight or less, based on 1 part by weight of the active ingredient, the solubility increases; however, when the amount exceeds 4 parts by weight, gelation of the solid dispersions occurs, thereby preventing the release of the active ingredient.

The solid dispersion of the present invention may further comprise an acid besides the active ingredient so as to enhance the solubility of the tetrazole derivative of the formula (I) or a pharmaceutically acceptable salt thereof. The acid may improve the solubility of the active ingredient by forming complex salts, adjusting pH value of the area surrounding the main ingredients, etc. Examples of the acid which can be used for the preparation of the solid dispersion of the invention include inorganic acids such as phosphoric acid, hydrochloric acid, sulfuric acid, nitric acid, acetic acid, boric acid and the like; and organic acids such as citric acid, malic acid, tartaric acid, lactic acid, tosilate, succinic acid, ascorbic acid, glutamic acid, alginic acid, maleic acid, adipic acid and the like. The degree of improvement in solubility may vary depending on the kind of the acid used. Particular examples of the acid in the present invention include phosphoric acid, malic acid, citric acid and tartaric acid. The acid may be included in an amount of 0.1 to 3 parts by weight, based on 1 part by weight of the active ingredient.

In accordance with one specific embodiment of the present invention, the solid dispersion comprising the tetrazole derivative of the formula (I) or a pharmaceutically acceptable salt thereof as an active ingredient may comprise a water-soluble polymer and an acid.

The solid dispersion in accordance with the present invention may be prepared by dissolving and dispersing the active ingredient in a mixed solution of methylene chloride, ethanol and distilled water. The ratio of the mixed solution methylene chloride:ethanol:distilled water is preferably 0.5 to 0.85 parts by weight:0.1 to 0.4 parts by weight:0.05 to 0.2 parts by weight, based on 1 part by weight of the total mixed solution. In accordance with one preferred embodiment, the weight ratio of the mixed solution methylene chloride:ethanol:distilled water is 60~80:20~40:2~10. In accordance with another preferred embodiment, the weight ratio of the mixed solution methylene chloride:ethanol:distilled water is 65~75:25~35:4~6. If the ratio of the mixed solution goes outside the said range, it may cause problems such as separation of layers or the main ingredients become insoluble in the solution.

The solid dispersion of the present invention has a small particle size, and thereby possesses an increased surface area. The average particle diameter of the solid dispersion of the present invention is less than 150 μm, preferably less than 100 μm, more preferably less than 40 μm.

The tetrazole derivative of the present invention is added with a water-soluble polymer or an acid to prepare an amorphous solid dispersion, thereby improving the solubility of the tetrazole derivative, and thus in vivo absorption rate of the said drug may be improved significantly.

The present invention provides a pharmaceutical composition comprising the said solid dispersion. The inventive pharmaceutical composition is effective for reducing MDR in cancer cells compared with conventional pharmaceutical compositions which simply contain the tetrazole derivative of the formula (I) or a pharmaceutically acceptable salt thereof.

Also, the solid dispersion comprising the tetrazole derivative of the formula (I) or a pharmaceutically acceptable salt thereof in accordance with the present invention can enhance oral absorption of anti-cancer agents and improve anti-cancer activity against cancer cells and, thus, co-administration of an anti-cancer agent, preferably, an anti-cancer agent whose rate of oral absorption is limited due to P-glycoprotein, may be used to increase the therapeutic effects thereof. Therefore, the solid dispersion in accordance with the present invention may be co-administered with an anti-cancer agent to patients who have acquired chemoresistance to overcome MDR and treat multidrug resistant cancer.

Anti-cancer agents suitable for mixing with the solid dispersion in accordance with the present invention are not particularly limited; however, some of the examples include taxane-based agents such as paclitaxel and docetaxel; vinca alkaloid-based agents such as vincristine, vinblastine and vinorelbine; anthracycline-based agents such as daunomycin and doxorubicin; camptothecin-based agents such as topotecan and irinotecan; actinomycin; and etopocide, etc.

The pharmaceutical composition of the present invention may be formulated in accordance with conventional methods, and may be prepared in the form of oral formulations such as tablets, pills, powders, capsules, syrups, emulsions, microemulsions, and others, or formulation for parenteral injection, e.g., intramuscular, intravenous, or subcutaneous administration. The pharmaceutical composition of the present invention may comprise the inventive solid dispersion, and any possible carrier and excipient. If the pharmaceutical composition of the present invention is prepared in the form of oral formulation, examples of carriers or excipients include cellulose, calcium silicate, corn starch, lactose, sucrose, dextrose, calcium phosphate, stearic acid, magnesium stearate, calcium stearate, gelatin, talc, surfactants, suspending agents, emulsifiers, diluents and others. Also, if the pharmaceutical composition of the present invention is prepared in the form of injectable formulation, examples of carriers include water, saline, glucose solution, glucose solution analogs, alcohols, glycols, ether (e.g., polyethylene glycol 400), oils, fatty acids, fatty acid esters, glycerides or surfactants, suspending agents, emulsifiers, and others.

The pharmaceutical composition comprising the inventive solid dispersion may be formulated by any method known in the art and administered singly before or after the administration of an anti-cancer agent, or administered together with one or more anti-cancer agents. The mode of administration may be adjusted depending on various factors such as the symptoms of the patients, physical properties of anti-cancer agent, and the like.

The solid dispersion of the present invention may be administered via oral or parenteral mode of administration together with an anti-cancer agent to a mammal including human in the range of 0.1 to 100 mg/kg (body weight), based on the tetrazole derivative or a pharmaceutically acceptable salt thereof, so as to reduce MDR in cancer cells.

Hereinafter, the present invention is described more specifically by the following Examples, but these are provided for illustration purposes only, and the present invention is not limited thereto. Hereinafter, the term 'HM30181A,' as used herein, refers to the compound of formula (II), chromone-2-carboxylic acid [2-(2-{4-[2-(6,7-dimethoxy-3,4-di-hydro-1H-isoquinolin-2-yl)-ethyl]-phenyl}-2H-tetrazol-5-yl)-4,5- dimethoxyphenyl]amine mesylate, which is an example of the compound of formula (I) as disclosed in KR Pat. No. 10-0557093:

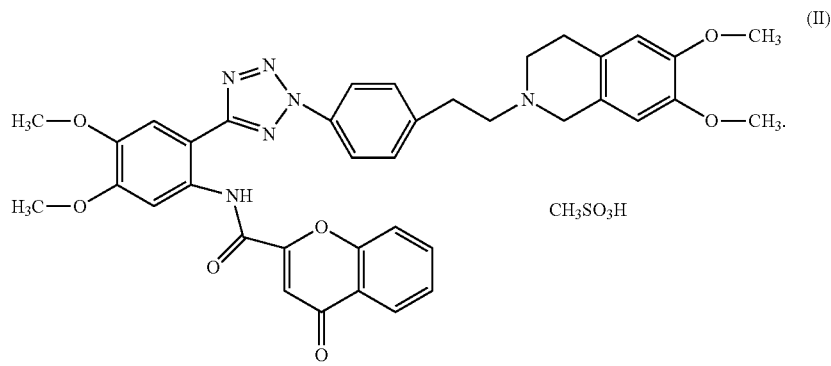

Example 1 to 6

Preparation of Solid Dispersion with Different Amount of Water-Soluble Polymer In accordance with the ingredients listed in Table 1, solid dispersions of Examples 1 to 6 were prepared by completely dissolving and dispersing HM30181A, as an active ingredient; hypromellose P-645, as a water-soluble polymer; and silicate, as an excipient, in a mixed solution of methylene chloride (MC), ethanol (EtOH) and distilled water (DW), and then spray drying the resulting solutions by using a mini spray dryer B-290 (Buchi, Switzerland).

TABLE 1

| Ingredient | Example 1 | Example 2 | Example 3 | Example 4 | Example 5 | Example 6 |
|---|---|---|---|---|---|---|
| HM30181A | 150 | 150 | 150 | 150 | 150 | 150 |
| Hypromellose P-645 | 0 | 75 | 150 | 300 | 450 | 600 |
| Silicate ($SiO_2$) | 0 | 150 | 150 | 150 | 150 | 150 |
| MC:EtOH:DW (6.5:3.0:0.5, w/w) | 9000 | 9000 | 9000 | 9000 | 9000 | 9000 |

Example 7 to 13

Preparation of Solid Dispersion with Different Kinds of Acid

In accordance with the ingredients listed in Table 2, solid dispersions of Examples 7 to 13 were prepared by completely dissolving and dispersing HM30181A, as an active ingredient; phosphoric acid, DL-malic acid, citric acid, L(+)-tartaric acid, fumaric acid or oxalic acid, as an acid; and hypromellose P-645, as a water-soluble polymer, in a mixed solution of MC, EtOH and DW, and then spray drying the resulting solutions by using a spray dryer.

TABLE 2

| Ingredient | Example 7 | Example 8 | Example 9 | Example 10 | Example 11 | Example 12 | Example 13 |
|---|---|---|---|---|---|---|---|
| HM30181A | 150 | 150 | 150 | 150 | 150 | 150 | 150 |
| Phosphoric acid | 100 | 150 | — | — | — | — | — |
| DL-malic acid | — | — | 300 | — | — | — | — |
| Citric acid | — | — | — | 300 | — | — | — |
| L(+)-tartaric acid | — | — | — | — | 300 | — | — |
| Fumaric acid | — | — | — | — | — | 300 | — |
| Oxalic acid | — | — | — | — | — | — | 300 |
| Hypromellose P-645 | 300 | 300 | 300 | 300 | 300 | 300 | 300 |
| MC:EtOH:DW (6.5:3.0:0.5, w/w) | 9000 | 9000 | 9000 | 9000 | 9000 | 9000 | 9000 |

Example 14

Preparation of a Tablet

In accordance with the ingredients listed in Table 3, a solid dispersion was prepared by completely dissolving and dispersing HM30181A, as an active ingredient; phosphoric acid, as an acid; and hypromellose P-645, as a water-soluble polymer, in a mixed solution of MC, EtOH and DW, and then spray drying the resulting solution by using a spray dryer.

Subsequently, in accordance with the ingredients listed in Table 4, a tablet of Example 14 was prepared by admixing the solid dispersion with D-mannitol, as an excipient; crospovidone, as a disintegrant; light anhydrous silicic acid, as an excipient; and sodium stearyl fumarate, as a lubricant, and then tabletizing the resulting mixture.

TABLE 3

| Ingredient | Amount (mg/tablet) |
|---|---|
| HM30181A | 60 |
| Phosphoric acid | 40 |
| Hypromellose P-645 | 60 |

TABLE 4

| Ingredient | Amount (mg/tablet) |
| --- | --- |
| Solid dispersion | 160 |
| D-mannitol (SD200) | 325 |
| Crospovidone | 50 |
| Light anhydrous silicic acid | 5 |
| Sodium stearyl fumarate | 10 |

Comparative Example 1

Preparation of a Tablet

In accordance with the ingredients listed in Table 5, a tablet of Comparative Example 1 was prepared by admixing HM30181A, as an active ingredient; phosphoric acid, as an acidic solubilizing agent; hypromellose P-645, as a water-soluble polymer; D-mannitol, as an excipient; crospovidone, as a disintegrant; light anhydrous silicic acid, as an excipient; and sodium stearyl fumarate, as a lubricant, and then tablet-izing the resulting mixture.

TABLE 5

| Ingredient | Amount (mg/tablet) |
| --- | --- |
| HM30181A | 60 |
| Phosphoric acid | 40 |
| Hypromellose P-645 | 60 |
| D-mannitol (SD200) | 325 |
| Crospovidone | 50 |
| Light anhydrous silicic acid | 5 |
| Sodium stearyl fumarate | 10 |

Test Example 1

Solubilities of Active Ingredient in Various Solvents

In order to find out the most suitable solvent for the solid dispersion, an excessive amount of HM30181A, as an active ingredient, was added to a solvent, shook for 2 hours, and then the resulting mixture was centrifuged and analyzed by HPLC to measure the solubility. Solvents used for solubility test were MC, methanol, EtOH, hexane, diethyl ether, isopropyl alcohol, acetone and DW. The results are shown in Table 6.

TABLE 6

| Solvent | Solubility (ppm) |
| --- | --- |
| Methylene chloride | 6848.28 |
| Methanol | 10177.50 |
| Ethanol | 382.63 |

TABLE 6-continued

| Solvent | Solubility (ppm) |
| --- | --- |
| Hexane | 0.05 |
| Diethyl ether | 0.00 |
| Isopropyl alcohol | 31.29 |
| Acetone | 9.23 |
| Distilled water | 0.00 |

As shown in Table 6 above, the solubilities of the tetrazole derivative, HM30181A, were low when it was dissolved in most of the solvents. The result indicates that if only one type of solvent is used in the preparation of the solid dispersion, then it would require a considerable amount of solvent for the solubilization of the active ingredient which may lead to reduced productivity as well as a rise in production costs.

Meanwhile, combinations of two solvents which resulted in good solubilities in the above solubility test, i.e., MC and EtOH, were prepared, and dissolution characteristics of HM30181A were observed. Methanol, which also showed a good solubility, was excluded in the test due to its toxicity. The results are shown in Table 7 below.

TABLE 7

| | HM30181A | Methylene chloride | Ethanol | Distilled water | Solution appearance | Solubility (ppm) |
| --- | --- | --- | --- | --- | --- | --- |
| Composition 1 (mg) | 15 | 450 | 50 | 0 | Clouded | 10,260 |
| Composition 2 (mg) | 15 | 350 | 150 | 0 | Clouded | 20,370 |
| Composition 3 (mg) | 15 | 250 | 250 | 0 | Clouded | 4,710 |
| Composition 4 (mg) | 15 | 450 | 50 | 25 | Separation of solvent layers | — |
| Composition 5 (mg) | 15 | 350 | 150 | 25 | Clear | 27,850 |

As shown in the Table above, it was confirmed that using a mixed solution of MC and EtOH which is added with DW was more advantageous than using a mixed solution of MC and EtOH only, because addition of DW enhanced solubilization of the active ingredient in a clear solution. Also, it can be concluded that the preferred weight ratio in the preparation of the mixed solvent for the solid dispersion was MC:EtOH:DW=70:30:5.

Test Example 2

Solubilities of Solid Dispersion Depending on Water-Soluble Polymer

The solid dispersions prepared in Examples 1 to 6 were assayed for dissolution by using suitable amounts of each sample which correspond to 150 mg of HM30181A, and then the solubilities were compared.

<Test Conditions>
Dissolution medium: distilled water, 900 mL
Test system: rotating sample container, 100 rpm
Temperature: 37° C.
<Analytical Conditions>
Column: stainless steel column (internal diameter of about 4.6 mm and length of 15 cm) packed with octadecylsilyl silica gel for LC (diameter of 5 μm)
Mobile phase: acetonitrile:pH 2.5 buffer (56:44)
Column temperature: 40° C.
Flow rate: 1.0 mL/min
Injection volume: 10 μL pH 2.5 buffer: 7.0 g of sodium perchlorate (NaClO$_4$) and 1.7 g of potassium dihydrogen phosphate (KH$_2$PO$_4$) were dissolved in 900 mL of distilled water, added with phosphoric acid to adjust the pH to 2.5, and then added with distilled water to make up a total volume of 1 L.

The solubilities of solid dispersions prepared in Examples 1 to 6 are shown in FIG. 1. As shown in FIG. 1, powder of solid dispersions, was not dissolved mostly in the solvent; however, when hypromellose (P-645), i.e., the water-soluble polymer, was added to the solvent, the solubility of the solid dispersion was improved. Also, it was observed that the solubility of the solid dispersion tends to increase as the amount of the water-soluble polymer increases. Particularly, the solubility was increased up to the point when the amount of the water-soluble polymer was four times the active ingredient; however, an amount exceeding four times the active ingredient caused gelation of the solid dispersions, thereby preventing the release of the active ingredient.

From the results above, it can be concluded that the most suitable amount of the water-soluble polymer for the solid dispersion of the present invention is in the range of from 0.1 to 4 parts by weight, based on 1 part by weight of the active ingredient.

Test Example 3

Solubilities of Solid Dispersion Depending on Acid

The solid dispersions prepared in Examples 7 to 13 were assayed for dissolution by using suitable amounts of each sample which correspond to 150 mg of HM30181A under the same conditions as described in Test Example 2. The results are shown in FIG. 2.

Figure 2:
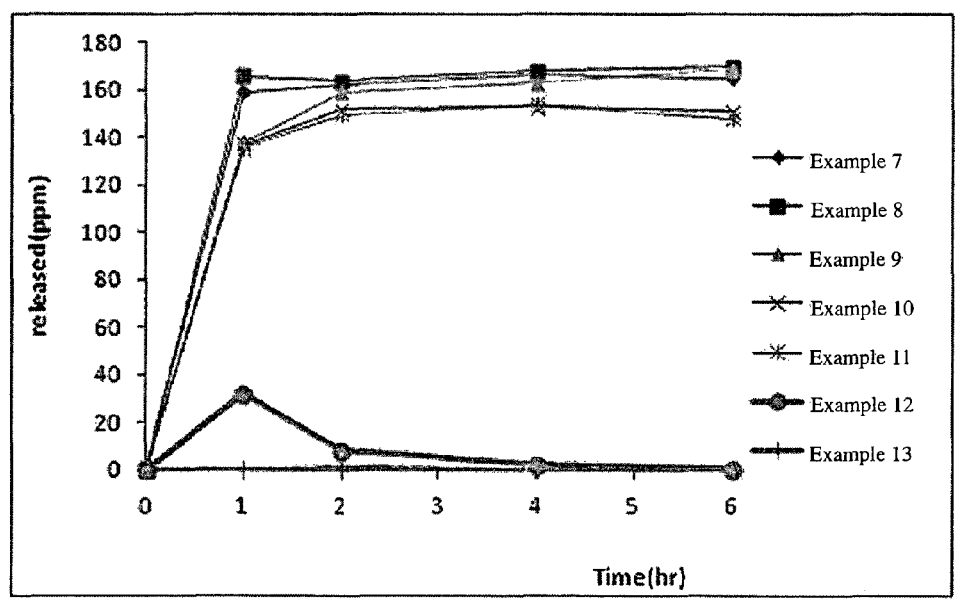
FIG. 2 is a graph showing the solubilities of the solid dispersions comprising HM30181A and different kinds of an acid (Examples 7 to 13).

As shown in FIG. 2, in the case when the solid dispersions were prepared by using phosphoric acid (Examples 7 and 8) and DL-malic acid (Example 9) as an acid, the solid dispersions which correspond to 150 mg of HM30181A were fully dissolved in 900 mL of DW, and the dissolved state was maintained for more than 24 hours, thus indicating the solid dispersions have good solubilities (FIG. 2 shows time progression up to 6 hours only). Also, in the case when the dispersions were prepared by using citric acid (Example 10) and L(+)-tartaric acid (Example 11), the solid dispersions which correspond to about 130 mg of HM30181A were dissolved in 900 mL of DW, thus indicating the solid dispersions have good solubilities.

Test Example 4

Analysis on the Crystalline Form of the Active Ingredient and the Solid Dispersions Comprising the Same X-ray diffraction patterns of the active ingredient, i.e., HM30181A, and the solid dispersion of Example 8 were determined by using M18XHF-SRA (Macsciences Co., LTD, Japan) under the conditions of Cu X-ray, 40 kV and 100 mA and scan speed of 6°/min.

Figure 3:
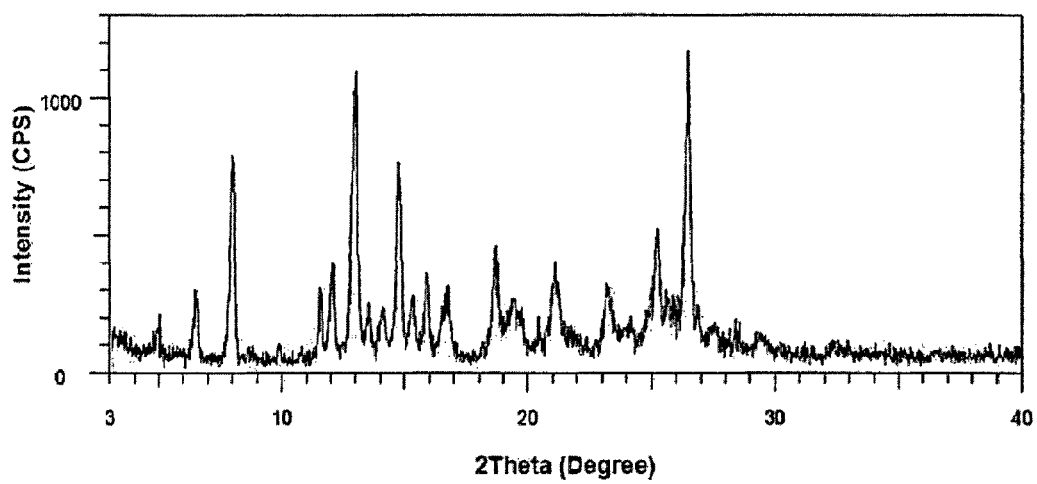
FIG. 3 shows the x-ray diffraction pattern of HM30181A.
Figure 4:
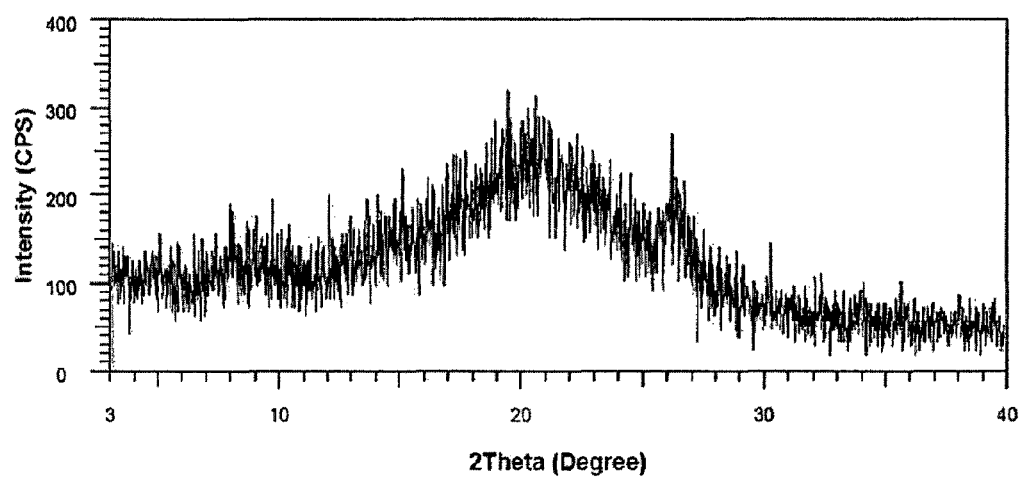
FIG. 4 shows the x-ray diffraction pattern of the solid dispersion of Example 8.

The results of X-ray diffraction patterns of HM30181A and the solid dispersion of Example 8 are shown in FIGS. 3 and 4, respectively. As shown in FIG. 3, the active ingredient, H30181A M, had peaks at two-theta (degree) 4.911, 6.474, 7.948, 9.827, 10.712, 11.522, 12.007, 12.936, 13.498, 14.063, 14.744, 15.282, 15.878, 16.686, 18.66, 19.388, 19.698, 21.065, 23.22, 25.222, 26.485, 26.86 and 28.405. However, as shown in FIG. 4, the solid dispersion comprising the active ingredient had become amorphous via spray drying process.

Test Example 5

Analysis on Particle Size of the Solid Dispersions

The average particle size of the solid dispersions of Examples 1 to 13 was measured by laser diffraction using a HELOS/BR (Sypatec, Germany) with a R1 lens under 4.5 bar conditions.

The results are shown in Table 8 below.

TABLE 8

| | Average particle size |
|---|---|
| Example 1 | 8 μm |
| Example 2 | 21 μm |
| Example 3 | 18 μm |
| Example 4 | 30 μm |
| Example 5 | 25 μm |
| Example 6 | 33 μm |
| Example 7 | 23 μm |
| Example 8 | 26 μm |
| Example 9 | 31 μm |
| Example 10 | 29 μm |
| Example 11 | 27 μm |
| Example 12 | 23 μm |
| Example 13 | 21 μm |

As shown in Table 8 above, the solid dispersions of Examples 1 to 13 had an average particle size of 30 μm or less.

Test Example 6

Analysis on Dissolution Properties of Tablets

The tablets prepared in Comparative Example 1 and Example 14 were assayed for dissolution and compared.
<Test Conditions>
Dissolution medium: distilled water, 900 mL
Test system: paddle, 100 rpm
Temperature: 37° C.
<Analytical Conditions>
Same as the conditions of Test Example 2

Figure 5:
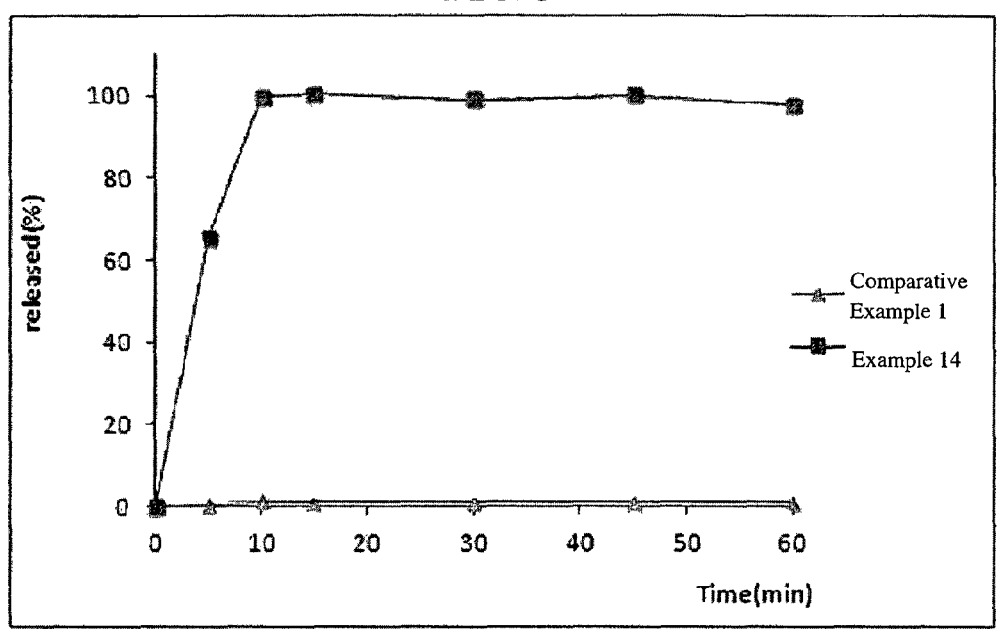
FIG. 5 is a graph showing the dissolution of the tablet of Example 14 prepared by using the inventive solid dispersion and the tablet of Comparative Example 1 prepared by simply mixing with the ingredients.

The results are shown in FIG. 5. As shown in FIG. 5, the tablet of Example 14 prepared by using the solid dispersion was completely dissolved within 15 minutes; however, the tablet of Comparative Example 1 which was prepared by simply mixing with the ingredients did not dissolve at all as time progressed. This result indicates that the solubility of the tetrazole derivative of the present invention cannot be improved if a tablet was prepared by simply mixing the tetrazole derivative with excipients: rather, the solubility can be improved by using the solid dispersion.

What is claimed is:
1. An amorphous solid dispersion comprising a tetrazole compound of the formula (I) or a pharmaceutically acceptable salt thereof as an active ingredient:

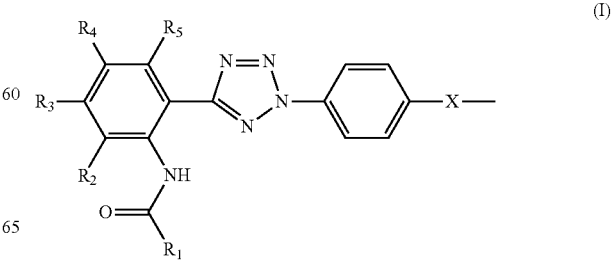

(I)

-continued

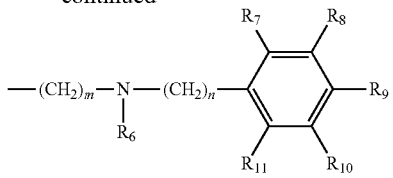

wherein,
R₁ is quinoline, isoquinoline, quinoxaline, pyridine, pyrazine, naphthalene, phenyl, thiophene, furan, 4-oxo-4H-chromene or cinnoline, which is unsubstituted or substituted by $C_1$-$C_5$alkyl, hydroxyl, $C_{1-5}$alkoxy, halogen, trifluoromethyl, nitro or amino;
$R_2$ to $R_5$ and $R_8$ to $R_{11}$ are each independently H, hydroxyl, halogen, nitro, $C_1$-$C_5$alkyl or $C_{1-5}$alkoxy; $R_6$ and $R_7$ are each independently H, hydroxyl, halogen, nitro, $C_{1-5}$alkylene or $C_{1-5}$ alkoxy; and $R_6$ and $R_7$ may be connected to form a 4- to 8-membered ring;
m and n are each independently integers ranging from 0 to 4; and
X is $CH_2$, O or S.

2. The amorphous solid dispersion of claim 1, wherein the tetrazole compound is the compound of formula (II) or (III):

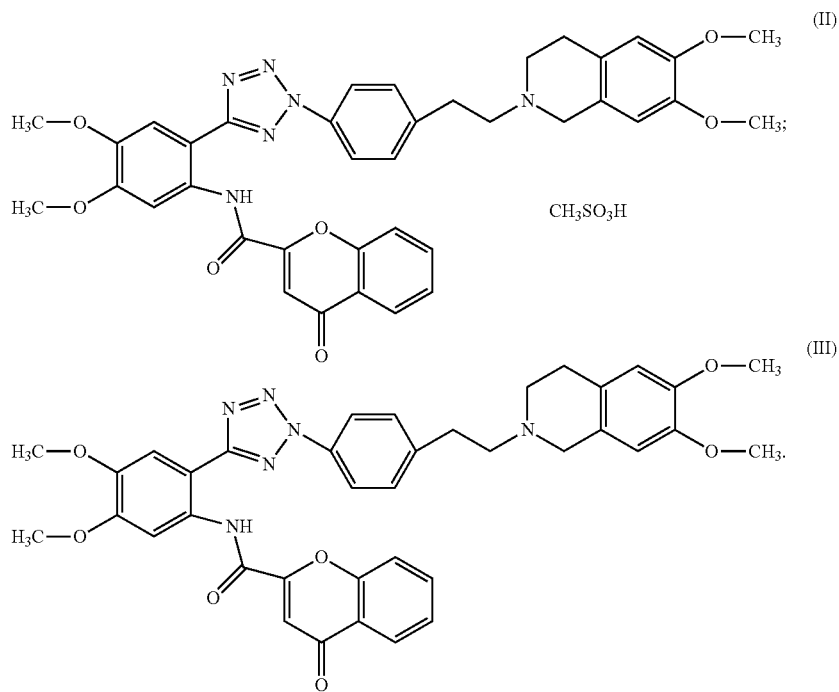

3. The amorphous solid dispersion of claim 1, wherein the solid dispersion further comprises a water-soluble polymer.

4. The amorphous solid dispersion of claim 3, wherein the water-soluble polymer is selected from the group consisting of hypromellose, hydroxypropyl cellulose, polyvinylpyrrolidone, polyvinyl acetal, diethyl aminoacetate, polyethylene glycol and a mixture thereof.

5. The amorphous solid dispersion of claim 3, wherein the water-soluble polymer is included in an amount of 0.1 to 4 parts by weight, based on 1 part by weight of the active ingredient.

6. The amorphous solid dispersion of claim 1, wherein the solid dispersion comprises an acid.

7. The amorphous solid dispersion of claim 6, wherein the acid is selected from the group consisting of an inorganic acid such as phosphoric acid, hydrochloric acid, sulfuric acid, nitric acid, acetic acid, boric acid; and an organic acid such as citric acid, malic acid, tartaric acid, lactic acid, tosilate, succinic acid, ascorbic acid, glutamic acid, alginic acid, maleic acid, adipic acid.

8. The amorphous solid dispersion of claim 6, wherein the acid is included in an amount of 0.1 to 3 parts by weight, based on 1 part by weight of the active ingredient.

9. The amorphous solid dispersion of claim 1, wherein the solid dispersion is prepared by using a mixed solution of methylene chloride, ethanol and distilled water in a ratio of methylene chloride:ethanol:distilled water=0.5 to 0.85 parts by weight:0.1 to 0.4 parts by weight:0.05 to 0.2 parts by weight.

10. The amorphous solid dispersion of claim 1, wherein the average particle diameter of the solid dispersion is less than 150 μm.

11. A pharmaceutical composition comprising the solid dispersion of claim 1.

12. The pharmaceutical composition of claim 11, wherein the pharmaceutical composition is used to reduce multi-drug resistance in cancer cells.

13. A pharmaceutical composition comprising the solid dispersion of claim 1 and an anti-cancer agent.

14. The pharmaceutical composition of claim 13, wherein the anti-cancer agent is selected from the group consisting of paclitaxel, docetaxel, vincristine, vinblastine, vinorelbine, daunomycin, doxorubicin, topotecan, irinotecan, actinomycin and etopocide.

15. A polymorph of a compound of formula (II), showing an X-ray power diffraction pattern comprising peaks at approximately 7.948, 12.936, 14.744, and 26.485 degree two-theta:

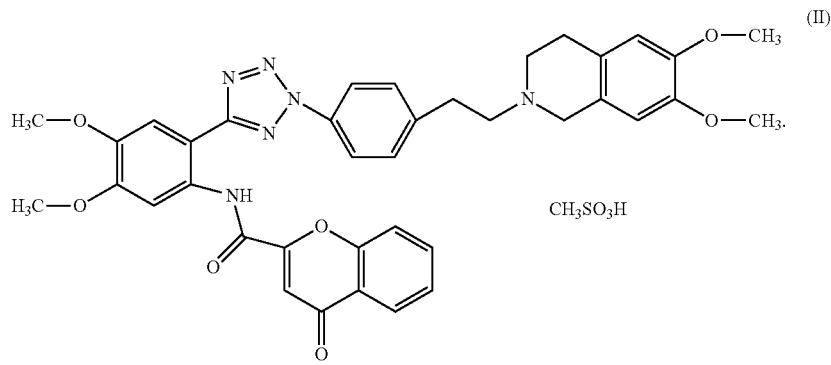

16. The polymorph of claim 15, showing an X-ray power diffraction pattern comprising peaks at approximately 4.911, 6.474, 7.948, 9.827, 10.712, 11.522, 12.007, 12.936, 13.498, 14.063, 14.744, 15.282, 15.878, 16.686, 18.66, 19.388, 19.698, 21.065, 23.22, 25.222, 26.485, 26.86 and 28.405 degree two-theta.

17. The polymorph of claim 15, showing an X-ray power diffraction pattern substantially similar to the X-ray power diffraction pattern set forth in FIG. 3.

18. A solid dispersion comprising the polymorph of claim 15.

19. A pharmaceutical composition comprising the polymorph of claim 15, and a pharmaceutically acceptable carrier.

20. A method for manufacturing a medicament for inhibiting a P-glycoprotein, comprising combining the polymorph of claim 15 and a pharmaceutically acceptable carrier to produce the medicament.

* * * * *